United States Patent

Whiteside

[11] Patent Number: 5,328,444
[45] Date of Patent: Jul. 12, 1994

[54] ORTHOTIC DEVICE FOR LIMITING LIMB MOTION AT A JOINT

[76] Inventor: Stacey A. Whiteside, 6810 S. Carney Ave., Tempe, Ariz. 85283

[21] Appl. No.: 16,306

[22] Filed: Feb. 11, 1993

[51] Int. Cl.⁵ .............................................. A61F 5/00
[52] U.S. Cl. ...................................... 602/16; 602/27; 16/375
[58] Field of Search .................. 602/5, 16, 20, 21, 23, 602/26–29; 16/374–377

[56] References Cited

U.S. PATENT DOCUMENTS

| | | |
|---|---|---|
| 3,970,305 | 7/1976 | Hawkins . |
| 4,254,953 | 3/1981 | Marchetti . |
| 4,353,361 | 10/1982 | Foster . |
| 4,604,997 | 8/1986 | DeBastiani et al. . |
| 4,881,299 | 11/1989 | Young et al. ..................... 16/375 X |
| 4,919,118 | 4/1990 | Morris . |
| 4,934,075 | 6/1990 | Benetti et al. . |
| 4,958,643 | 9/1990 | Pansiera ........................... 16/375 X |
| 5,022,390 | 6/1991 | Whiteside ............................. 602/27 |
| 5,044,360 | 9/1991 | Janke .................................... 602/27 |
| 5,187,837 | 2/1993 | Gunderson et al. ................. 16/375 |

Primary Examiner—Richard J. Apley
Assistant Examiner—Linda C. M. Dvorak
Attorney, Agent, or Firm—Cahill, Sutton & Thomas

[57] ABSTRACT

The motion of two pivotally connected orthosis members are limited in both directions of movement. An adjustable arresting member limits motion in one direction. An elongated member, preferably made of flexible cables, is connected to the two orthosis members to limit motion in the opposite direction.

8 Claims, 2 Drawing Sheets

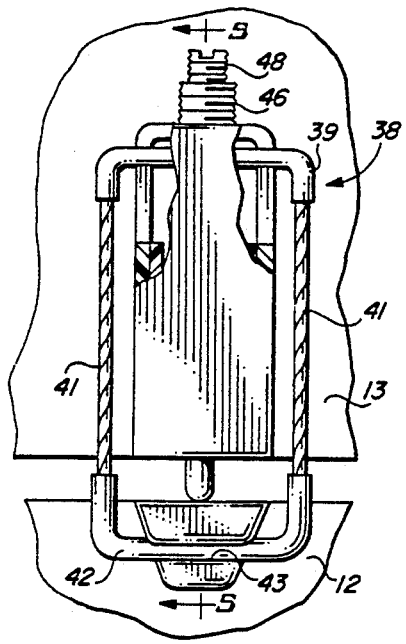
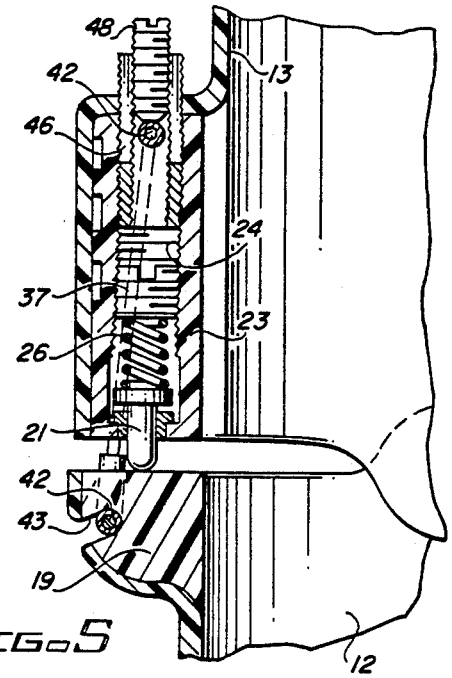
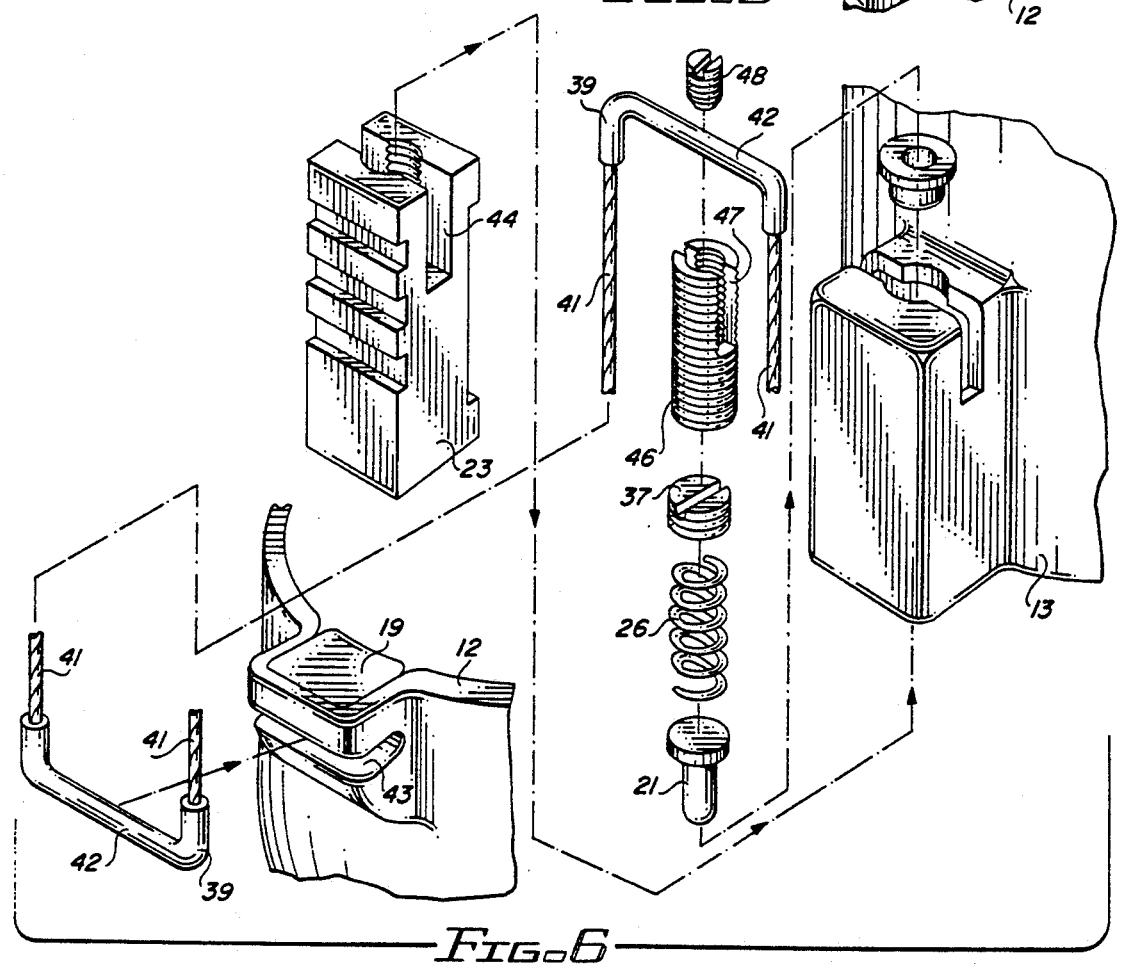

ORTHOTIC DEVICE FOR LIMITING LIMB MOTION AT A JOINT

TECHNICAL FIELD

This invention relates to orthotic devices generally and particularly to an ankle-foot orthosis with adjustable controlled motion.

BACKGROUND ART

U.S. Pat. No. 5,022,390 was granted to the present applicant on Jun. 11, 1991, for an "Orthotic Device for Limiting Limb Motion at a Joint". That patent discloses an ankle-foot orthosis with an adjustable stop mechanism for limiting downward motion of the foot. No provision was made in that orthosis for limiting foot motion in the opposite direction.

An ankle-foot orthosis with provision for adjustably controlling the range of motion of the foot in both directions is disclosed in U.S. Pat. No. 5,044,360, granted Sep. 3, 1991, to W. R. Janke for "Orthosis With Variable Motion Controls". Adjustments to the range of motion permitted requires replacement of pairs of cam members in an ankle joint assembly of the appliance.

There continues to be a need for an orthosis with provisions for easily and reliably adjusting limb motion in both directions.

DISCLOSURE OF THE INVENTION

This invention contemplates utilizing an arresting mechanism quite similar to that disclosed and claimed in applicant's prior U.S. Pat. No. 5,022,390 for arresting and stopping movement of the limb in one direction. But this mechanism is supplemented by an elongated cable member connected to the two limb-engaging members of the orthosis for limiting limb motion in the opposite direction. The latter mechanism includes means carried by one of the limb members for adjusting the effective length of the cable member. Child and adult mechanisms are disclosed.

BRIEF DESCRIPTION OF THE DRAWINGS

The invention is described in greater detail hereinafter by reference to the accompanying drawings, wherein:

FIG. 4 is a fragmentary rear view of modified arresting and stop mechanisms employed in another embodiment of the invention;

FIG. 5 is a vertical sectional view of the modified arresting and stop mechanisms taken as indicated by line 5—5 in FIG. 4; and FIG. 6 is an exploded perspective view of the arresting and stop mechanisms of FIGS. 4 and 5.

BEST MODES FOR CARRYING OUT THE INVENTION

Figure 1:
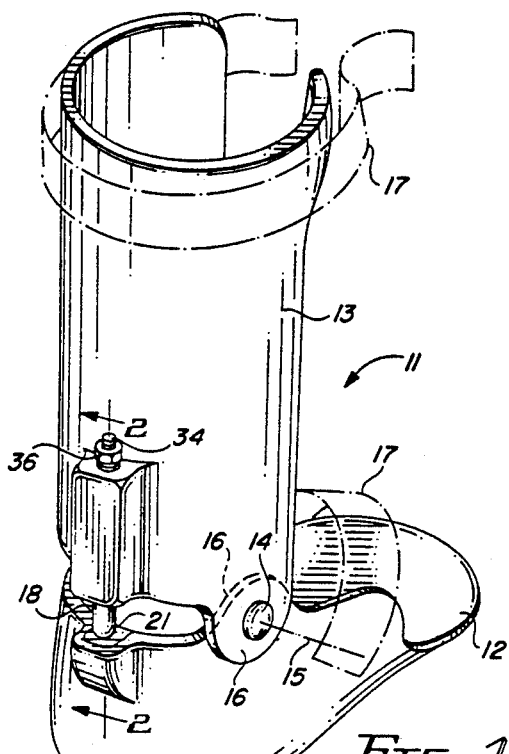
FIG. 1 is a perspective view of an orthotic device embodying the invention.
Figure 2:
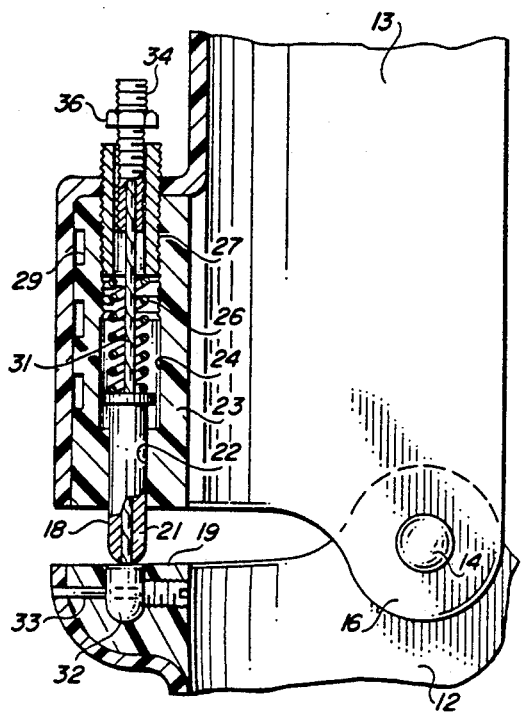
FIG. 2 is an enlarged, fragmentary, vertical sectional view of the arresting and stop mechanisms of the device, taken as indicated by the line 2—2 in FIG. 1.

Referring particularly to FIGS. 1 and 2, the orthotic device, or orthosis, there illustrated is identified generally by reference numeral 11. This particular device is designed specifically to control motion of a foot about an ankle joint, neither of which limb members are shown in the drawings. It is to be understood, however, that the principles of construction of orthosis 11 and the invention embodied therein are applicable to control movement of other limbs about other joints of the human anatomy.

Basically, the orthosis 11 is comprised of two members, 12 and 13, pivotally connected at 14 for angular movement about an axis 15 which is substantially coextensive with the major horizontal axis of the wearer's ankle joint.

Each of the members 12 and 13 is configured to have its inner surface in conformance with that portion of the anatomy to which it is to be secured. First member 12 is configured to closely receive and contact the surface of the heel and rear instep portion of the wearer's foot. Second member 13 is configured to closely receive and contact the wearer's lower calf. Overlapping tab regions 16 of members 12 and 13 receive rivets which provide the pivotal connection 14 between the members. Flexible straps (shown in phantom at 17) with fabric hook and loop fasteners may be employed to hold the members 12 and 13 in position on the limbs.

Orthosis members 12 and 13 are preferably formed of thermoplastic sheet material, such as polypropylene or a mixture of polypropylene and polyethylene. Such materials can be easily vacuum-thermo-formed into intricate configurations, are quite strong, and are semi-flexible so they are comfortable when worn in contact with parts of the body.

Fabricating members 12 and 13 first requires that casts be made of the wearer's limbs and from these casts male molds are made in the configurations of the limbs. Warm sheets of plastic are draped over the male molds and a vacuum applied therebeneath to pull the sheets over and into intimate contact with the molds. After being cooled, the members 12 and 13 are trimmed to the desired peripheral configurations.

As with most orthotic appliances, it is desirable to limit the extent of pivotal movement of members 12 and 13. For limiting the extent to which the foot can be tilted downwardly about the ankle, orthosis 11 is equipped with adjustable arresting means, or mechanism, indicated generally by reference number 18.

Figure 3:
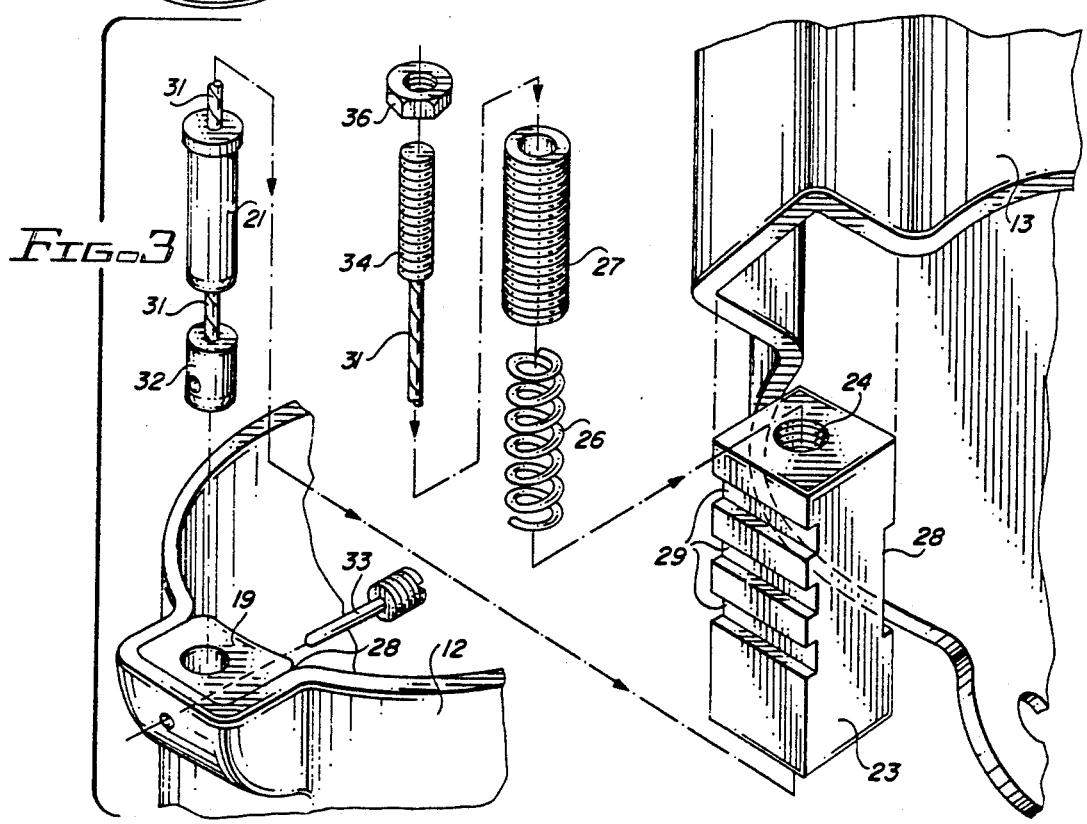
FIG. 3 is an exploded perspective view of the arresting and stop mechanisms shown in FIG. 2.

The components of the adjustable arresting mechanism 18 are shown in greater detail in FIGS. 2 and 3, and include an abutment 19 carried by the first, or foot, member 12 and a movable plunger 21 carried by the second, or leg, member 13. Plunger 21 is slidingly received in a bore 22 in a mounting block 23 secured to member 13.

Mounting block 23 also has an enlarged bore 24 extending upwardly from the upper end of plunger 21 to house a helical compression spring 26 and a threaded cylinder 27. Cylinder 27 is threadably received in mounting block bore 24 and, therefore, is adjustable up and down to adjust the compression of spring 26 and, consequently, the resistance offered to upward movement of arresting plunger 21.

Arresting mechanism 18 is preferably installed in the orthosis members 12 and 13 as the latter are thermoformed. This is done by temporarily affixing the abutment 19 and the mounting block 23 in appropriate positions on the male molds before the plastic sheets are thermo-formed over these molds. The abutment 19 is placed on the mold portion forming the upper reach of member 12. The mounting block 23 is positioned on the mold for member 13 near the lower rear edge of the latter member.

Abutment 19 is fixed in place in the foot member 12 and the mounting block is fixed in place in the leg member 13. This is assured by providing corner indentations 28 in the forward corners of both the abutment and the mounting block (see FIG. 3). In addition, it is desirable to provide additional indentations 29 in the rear face of mounting block 23 to prevent vertical displacement of the block during use of the orthosis. When the plastic sheets are drawn down onto the molds and over the mounting block 23 and the abutment 19, the plastic flows into the indentations 28 and 29 in these components to lock them firmly in place.

It can be appreciated that adjustment of threaded cylinder 27 can adjust the arresting force applied by plunger 21 to abutment 19 to arrest movement of the foot member 12 downwardly with reference to the leg member 13. If the position of threaded cylinder 27 is such that the spring 26 is fully compressed, i.e., bottomed out, the plunger 21 can move no farther and acts as a positive stop for the foot member 12 in one direction of movement. The arresting mechanism 18 thus acts as an adjustable stop in the same manner as the adjustable stop mechanism disclosed and claimed in applicant's '390 patent. The present invention supplements this arresting mechanism with adjustable stop means for limiting relative motion of the orthosis members 12 and 13 in the opposite direction.

The adjustable stop means for this direction of movement utilizes an elongated member 31 which is connected to and extends between orthosis members 12 and 13. Elongated member 31 is preferably a flexible cable made of braided steel wire. Member 31 has secured to its lower end an anchor 32 which is embedded in and secured in place in abutment 19 by a locking pin 33 passing through complementary bores in the abutment and the anchor.

Elongated member 31 extends upwardly through a passage provided therefor in plunger 21, through helical spring 26, through mounting block bore 24 and through the interior of threaded cylinder 27. The top end of the elongated member 31 has a threaded extension 34 adapted to carry a nut 36 which serves as a keeper member for the upper end of elongated member 31.

Keeper nut 36 is positioned to abut the upper end of threaded cylinder 27 to effectively limit the effective length of elongated member 31 and therefore effectively limit the extent of movement of member 12 relative to member 13. Adjustment of keeper nut 36 on extension 34 adjusts the amount of motion permitted.

The arresting and adjustable stop means just described is entirely satisfactory for orthotic devices used by children and small adults. However, for large and heavy adults the forces generated in use of the appliance may be too great to be withstood by the single strand elongated stop member 31. For such applications, the arresting and adjustable stop means may take the form illustrated in FIGS. 4–6.

Referring specifically to those figures, the reference numerals 12 and 13 again designate the foot and leg members, respectively, of the orthosis. As in the previous embodiment of the invention, these members carry an abutment 19 and a mounting block 23. Housed within the mounting block 23 is an arresting plunger 21 which is biased downwardly by a spring 26 within a threaded bore 24 in the block. The force exerted by spring 26 on plunger 21 is adjusted by turning a set screw 37 threadably received in bore 24 and bearing on the upper end of the spring. The function of this arresting mechanism is the same as that described above for the embodiment illustrated in FIGS. 1–3.

In the embodiment of FIGS. 4–6, however, the adjustable stop mechanism, indicated generally by reference numeral 38, is made stronger to withstand the forces generated by an adult user of the orthosis. Stop mechanism 38 employs an elongated member 39 which is connected to foot member 12 and to leg member 13 to limit relative movement of these members. For strength, the elongated member 39 is formed by a pair of wire cables 41 which extend alongside, but outside, mounting block 23. Cables 41 are fastened at each end to a U-shaped yoke 42. The lower yoke 42 is received in a transverse slot 43 provided therefor in abutment 19 on member 12. The upper yoke 42 resides in a vertical slot 44 provided therefor in mounting block 23 carried by member 13.

The adjustable stop mechanism 38 also includes means for adjusting the effective length of elongated member 39 to adjust the range of movement of orthosis members 12 and 13. This adjusting means includes an internally and externally threaded cylinder 46 which is slotted at 47 to receive upper yoke 42 of the elongated member 39. With the elongated member removed from cylinder 46, the latter can be turned within bore 24 of block 23 to raise or lower the position of the cylinder in the mounting block 23. In this manner, the cylinder 46 functions as an adjustable keeper means to adjust the effective length of the elongated stop member 39. A retainer screw 48 threaded into the upper end of cylinder 46 is employed to retain the upper yoke 42 of the elongated member in place in the slotted region 47 of the cylinder.

It can be appreciated that the adjustable stop mechanism 38 of the embodiment of the invention illustrated in FIGS. 4–6 and described above has considerable strength by virtue of employing a pair of cables 41 to form the elongated stop member 30.

What is claimed is:

1. An orthotic device for a limb joint, said device comprising first and second members adapted, respectively, to be attached to portions of the anatomy on opposite sides of the joint, a pivotal connection between said first and second members, said pivotal connection having an axis substantially corresponding to an axis of motion of the joint, an abutment carried by said first member, an adjustable arresting member carried by said second member and engagable with said abutment for arresting pivotal movement between said first and second members in one direction about the pivotal axis, means carried by said second member for adjusting said arresting member, and means for adjustably limiting pivotal movement between said first and second members in the opposite direction about the pivotal axis, said limiting means comprising an elongated member engagable with said first and second members, said elongated member comprising flexible.

2. The orthotic device of claim 1, further characterized in that said second member has thereon means for adjusting the effective length of said elongated member.

3. The orthotic device of claim 2, wherein the means for adjusting the effective length of said elongate member is movable keeper means carried by said second member.

4. The orthotic device of claim 1, further characterized in that said flexible cable means has one end attached to said first member and said second member has adjustable keeper means thereon operatively associated with the opposite end of the cable means.

5. An orthotic device for a limb joint, said device comprising first and second members adapted, respectively, to be attached to portions of the anatomy on opposite sides of the joint, a pivotal connection between said first and second members, said pivotal connection having an axis substantially corresponding to an axis of motion of the joint, an abutment carried by said first member, a mounting block carried by said second member, an adjustable arresting member slidably carried by said mounting block and engagable with said abutment for arresting pivotal movement of said first and second members in one direction, an adjusting member threadably received in said mounting block and adapted to adjust said arresting member, said arresting member and said adjusting member having openings therethrough, a flexible cable member having one end thereof attached to said abutment, said cable member extending through the openings in said arresting member and said adjusting member, and an adjustable keeper member on the other end of said cable member for adjusting the effective length of said cable member in relation to said first and second members, said cable member serving to limit pivotal movement of said first and second members in the opposite direction.

6. The orthotic device of claim 5, further comprising a compression spring positioned between said arresting member and said adjusting member for biasing said arresting member toward said abutment.

7. An orthotic device for a limb joint, said device comprising first and second members adapted, respectively, to be attached to portions of the anatomy on opposite sides of the joint, a pivotal connection between said first and second members, said pivotal connection having an axis substantially corresponding to an axis of motion of a joint, an abutment carried by said first member, a mounting block carried by said second member, an adjustable arresting member slidably carried by said mounting block and engagable with said abutment for arresting pivotal movement of said first and second members in one direction, an adjusting member threadably received in said mounting block and adapted to adjust said arresting member, a pair of flexible cables, each having one end attached to said first member, said flexible cables extending along opposite sides of said mounting block, and an adjustable keeper member carried by said mounting block for adjustably positioning the other end of each cable, said cables serving to limit pivotal movement of said first and second members in the opposite direction.

8. The orthotic device of claim 7, further comprising a compression spring positioned between said arresting member and said adjusting member for biasing said arresting member toward said abutment.

* * * * *